(12) United States Patent
Nierenberg et al.

(10) Patent No.: US 11,317,871 B2
(45) Date of Patent: May 3, 2022

(54) METHOD AND SYSTEM FOR DETECTING AND REMOVING EEG ARTIFACTS

(71) Applicant: Persyst Development Corporation, San Diego, CA (US)

(72) Inventors: Nicolas Nierenberg, La Jolla, CA (US); Scott B. Wilson, Del Mar, CA (US); Mark L. Scheuer, Wexford, PA (US)

(73) Assignee: Persyst Development Corporation, Solana Beach, CA (US)

( * ) Notice: Subject to any disclaimer, the term of this patent is extended or adjusted under 35 U.S.C. 154(b) by 279 days.

(21) Appl. No.: 15/361,309

(22) Filed: Nov. 25, 2016

(65) Prior Publication Data

US 2017/0079593 A1 Mar. 23, 2017

Related U.S. Application Data

(63) Continuation of application No. 13/684,556, filed on Nov. 25, 2012, now abandoned.

(60) Provisional application No. 61/563,767, filed on Nov. 26, 2011.

(51) Int. Cl.

| | |
|---|---|
| *A61B 5/00* | (2006.01) |
| *A61B 5/0205* | (2006.01) |
| *A61B 5/291* | (2021.01) |
| *A61B 5/316* | (2021.01) |
| *A61B 5/369* | (2021.01) |
| *A61B 5/374* | (2021.01) |
| *A61B 5/11* | (2006.01) |

(52) U.S. Cl.
CPC .......... *A61B 5/7214* (2013.01); *A61B 5/0205* (2013.01); *A61B 5/1103* (2013.01); *A61B 5/291* (2021.01); *A61B 5/316* (2021.01); *A61B 5/369* (2021.01); *A61B 5/374* (2021.01); *A61B 5/4552* (2013.01); *A61B 5/7203* (2013.01)

(58) Field of Classification Search
None
See application file for complete search history.

(56) References Cited

U.S. PATENT DOCUMENTS

| | | |
|---|---|---|
| 4,550,736 A | 11/1985 | Broughton et al. |
| 4,644,956 A | 2/1987 | Morgenstern |
| 4,709,702 A | 12/1987 | Sherwin |
| 4,967,038 A | 10/1990 | Gevins et al. |
| 5,038,782 A | 8/1991 | Gevins et al. |
| 5,305,746 A | 4/1994 | Fendrock |
| 5,309,909 A | 5/1994 | Gadsby et al. |
| 5,626,145 A | 5/1997 | Clapp et al. |
| 5,846,208 A | 12/1998 | Pichlmayr et al. |
| 6,334,856 B1 | 1/2002 | Allen et al. |
| 6,591,132 B2 | 7/2003 | Gotman et al. |
| 6,931,274 B2 | 8/2005 | Williams |
| 7,286,871 B2 | 10/2007 | Cohen |
| 7,809,433 B2 | 10/2010 | Keenan |
| 7,941,201 B2 | 5/2011 | Chiou et al. |
| 8,112,141 B2 | 2/2012 | Wilson et al. |
| 8,694,070 B2 | 4/2014 | Wilson |
| 9,055,927 B2 | 6/2015 | Wilson et al. |
| 2002/0082551 A1 | 6/2002 | Ennen et al. |
| 2002/0099306 A1 | 7/2002 | Shaw et al. |
| 2004/0152957 A1 | 8/2004 | Stivoric et al. |
| 2005/0059874 A1 | 3/2005 | Fuchs et al. |
| 2007/0135727 A1 | 6/2007 | Virtanen et al. |
| 2007/0167858 A1 | 7/2007 | Virtanen et al. |
| 2008/0262335 A1 | 10/2008 | Sun et al. |
| 2009/0062680 A1 | 3/2009 | Sandford |
| 2009/0247895 A1 | 10/2009 | Morikawa et al. |
| 2009/0287107 A1 | 11/2009 | Beck-Nielsen et al. |
| 2011/0015503 A1 | 1/2011 | Joffe et al. |
| 2011/0178421 A1 | 7/2011 | Schultz |
| 2011/0224569 A1 | 9/2011 | Isenhart et al. |

FOREIGN PATENT DOCUMENTS

| | | |
|---|---|---|
| JP | 6023210 | 10/2016 |
| WO | WO2013078472 | 5/2013 |

OTHER PUBLICATIONS

Ruiz, Ricardo A. Salido, Radu Ranta, and Valerie Louis-Dorr. "EEG montage analysis in the Blind Source Separation framework." Biomedical signal processing and control 6.1 (2011): 77-84.*
Correa, A. Garcés, et al. "Artifact removal from EEG signals using adaptive filters in cascade." Journal of Physics: Conference Series. vol. 90. No. 1. IOP Publishing, 2007.*
International Search Report for PCT Application PCT/US2012/066480, dated Mar. 21, 2013.
International Preliminary Report on Patentability, dated Mar. 21, 2013.

* cited by examiner

*Primary Examiner* — G Steven Vanni

(74) *Attorney, Agent, or Firm* — Clause Eight; Michael Catania

(57) ABSTRACT

A method and system for detecting and removing EEG artifacts is disclosed herein. Each source of a plurality of sources for an EEG signal is separated for a selected artifact type. Each source of the plurality of sources is reconstituted into a recorded montage and an optimal reference montage for recognizing the selected artifact type of each source. The sources with artifacts are removed and the remaining sources are reconstituted into a filtered montage for the EEG signal.

1 Claim, 14 Drawing Sheets

METHOD AND SYSTEM FOR DETECTING AND REMOVING EEG ARTIFACTS

CROSS REFERENCE TO RELATED APPLICATION

The Present application is a continuation application of U.S. patent application Ser. No. 13/684,556, filed on Nov. 25, 2012, which claims priority to U.S. Provisional Patent Application No. 61/563,767, filed on Nov. 26, 2011, now expired, both of which are hereby incorporated by reference in their entireties.

STATEMENT REGARDING FEDERALLY SPONSORED RESEARCH OR DEVELOPMENT

Not Applicable

BACKGROUND OF THE INVENTION

Field of the Invention

The present invention generally relates to EEG recordings. More specifically, the present invention relates to detecting and filtering artifacts from an EEG recording.

Description of the Related Art

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these electric voltage fields create an electrical reading which electrodes on the person's head are able to detect and record. An EEG is a superposition of multiple simpler signals. In a normal adult, the amplitude of an EEG signal typically ranges from 1 micro-Volt to 100 micro-Volts, and the EEG signal is approximately 10 to 20 milli-Volts when measured with subdural electrodes. The monitoring of the amplitude and temporal dynamics of the electrical signals provides information about the underlying neural activity and medical conditions of the person.

An EEG is performed to: diagnose epilepsy; verify problems with loss of consciousness or dementia; verify brain activity for a person in a coma; study sleep disorders, monitor brain activity during surgery, and additional physical problems.

Multiple electrodes (typically 17-21, however there are standard positions for at least 70) are attached to a person's head during an EEG. The electrodes are referenced by the position of the electrode in relation to a lobe or area of a person's brain. The references are as follows: F=frontal; Fp=frontopolar; T=temporal; C=central; P=parietal; O=occipital; and A=auricular (ear electrode). Numerals are used to further narrow the position and "z" points relate to electrode sites in the midline of a person's head. An electrocardiogram ("EKG") may also appear on an EEG display.

The EEG records brain waves from different amplifiers using various combinations of electrodes called montages. Montages are generally created to provide a clear picture of the spatial distribution of the EEG across the cortex. A montage is an electrical map obtained from a spatial array of recording electrodes and preferably refers to a particular combination of electrodes examined at a particular point in time.

In bipolar montages, consecutive pairs of electrodes are linked by connecting the electrode input 2 of one channel to input 1 of the subsequent channel, so that adjacent channels have one electrode in common. The bipolar chains of electrodes may be connected going from front to back (longitudinal) or from left to right (transverse). In a bipolar montage signals between two active electrode sites are compared resulting in the difference in activity recorded. Another type of montage is the referential montage or monopolar montage. In a referential montage, various electrodes are connected to input 1 of each amplifier and a reference electrode is connected to input 2 of each amplifier. In a reference montage, signals are collected at an active electrode site and compared to a common reference electrode.

Reference montages are good for determining the true amplitude and morphology of a waveform. For temporal electrodes, CZ is usually a good scalp reference.

Being able to locate the origin of electrical activity ("localization") is critical to being able to analyze the EEG. Localization of normal or abnormal brain waves in bipolar montages is usually accomplished by identifying "phase reversal," a deflection of the two channels within a chain pointing to opposite directions. In a referential montage, all channels may show deflections in the same direction. If the electrical activity at the active electrodes is positive when compared to the activity at the reference electrode, the deflection will be downward. Electrodes where the electrical activity is the same as at the reference electrode will not show any deflection. In general, the electrode with the largest upward deflection represents the maximum negative activity in a referential montage.

Some patterns indicate a tendency toward seizures in a person. A physician may refer to these waves as "epileptiform abnormalities" or "epilepsy waves." These include spikes, sharp waves, and spike-and-wave discharges. Spikes and sharp waves in a specific area of the brain, such as the left temporal lobe, indicate that partial seizures might possibly come from that area. Primary generalized epilepsy, on the other hand, is suggested by spike-and-wave discharges that are widely spread over both hemispheres of the brain, especially if they begin in both hemispheres at the same time.

There are several types of brain waves: alpha waves, beta waves, delta wave, theta waves and gamma waves. Alpha waves have a frequency of 8 to 12 Hertz ("Hz"). Alpha waves are normally found when a person is relaxed or in a waking state when a person's eyes are closed but the person is mentally alert. Alpha waves cease when a person's eyes are open or the person is concentrating. Beta waves have a frequency of 13 Hz to 30 Hz. Beta waves are normally found when a person is alert, thinking, agitated, or has taken high doses of certain medicines. Delta waves have a frequency of less than 3 Hz. Delta waves are normally found only when a person is asleep (non-REM or dreamless sleep) or the person is a young child. Theta waves have a frequency of 4 Hz to 7 Hz. Theta waves are normally found only when the person is asleep (dream or REM sleep) or the person is a young child. Gamma waves have a frequency of 30 Hz to 100 Hz. Gamma waves are normally found during higher mental activity and motor functions.

The following definitions are used herein.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

"Artifacts" are electrical signals detected along the scalp by an EEG, but that originate from non-cerebral origin. There are patient related artifacts (e.g., movement, sweating, ECG, eye movements) and technical artifacts (50/60 Hz artifact, cable movements, electrode paste-related).

The term "differential amplifier" refers to the key to electrophysiological equipment. It magnifies the difference between two inputs (one amplifier per pair of electrodes).

"Duration" is the time interval from the beginning of the voltage change to its return to the baseline. It is also a measurement of the synchronous activation of neurons involved in the component generation.

"Electrode" refers to a conductor used to establish electrical contact with a nonmetallic part of a circuit. EEG electrodes are small metal discs usually made of stainless steel, tin, gold or silver covered with a silver chloride coating. They are placed on the scalp in special positions.

"Electrode gel" acts as a malleable extension of the electrode, so that the movement of the electrodes leads is less likely to produce artifacts. The gel maximizes skin contact and allows for a low-resistance recording through the skin.

The term "electrode positioning" (10/20 system) refers to the standardized placement of scalp electrodes for a classical EEG recording. The essence of this system is the distance in percentages of the 10/20 range between Nasion-Inion and fixed points. These points are marked as the Frontal pole (Fp), Central (C), Parietal (P), occipital (O), and Temporal (T). The midline electrodes are marked with a subscript z, which stands for zero. The odd numbers are used as subscript for points over the left hemisphere, and even numbers over the right "Electroencephalogram" or "EEG" refers to the tracing of brain waves, by recording the electrical activity of the brain from the scalp, made by an electroencephalograph.

"Electroencephalograph" refers to an apparatus for detecting and recording brain waves (also called encephalograph).

"Epileptiform" refers to resembling that of epilepsy.

"Filtering" refers to a process that removes unwanted frequencies from a signal.

"Filters" are devices that alter the frequency composition of the signal.

"Montage" means the placement of the electrodes. The EEG can be monitored with either a bipolar montage or a referential one. Bipolar means that there are two electrodes per one channel, so there is a reference electrode for each channel. The referential montage means that there is a common reference electrode for all the channels.

"Morphology" refers to the shape of the waveform. The shape of a wave or an EEG pattern is determined by the frequencies that combine to make up the waveform and by their phase and voltage relationships. Wave patterns can be described as being: "Monomorphic". Distinct EEG activity appearing to be composed of one dominant activity. "Polymorphic". distinct EEG activity composed of multiple frequencies that combine to form a complex waveform. "Sinusoidal". Waves resembling sine waves. Monomorphic activity usually is sinusoidal. "Transient". An isolated wave or pattern that is distinctly different from background activity.

"Spike" refers to a transient with a pointed peak and a duration from 20 to under 70 msec.

The term "sharp wave" refers to a transient with a pointed peak and duration of 70-200 msec.

The term "neural network algorithms" refers to algorithms that identify sharp transients that have a high probability of being epileptiform abnormalities.

"Noise" refers to any unwanted signal that modifies the desired signal. It can have multiple sources.

"Periodicity" refers to the distribution of patterns or elements in time (e.g., the appearance of a particular EEG activity at more or less regular intervals). The activity may be generalized, focal or lateralized.

An EEG epoch is an amplitude of a EEG signal as a function of time and frequency.

In order to optimize automated artifact removal from an EEG it is important to select an optimal montage as input and then use the resulting processed montage to produce the montages required by the user, or by additional signal processing algorithms. Published algorithms do not describe this process and either use the recorded montage as input or perform artifact removal directly on a single montage that a user has selected for viewing.

All digital EEG recordings are recorded as the difference between the various electrodes and a reference or ground electrode. This is called the recorded Montage. Mathematical transformation can then be used to produce any other Montage that is needed. When performing signal detection the recorded montage may not be the optimal starting point because of the location of the ground electrode. Instead the optimal starting point is frequently one using of the vertex electrodes as a reference such as one that is termed CZ in the international standard. However the CZ electrode may be compromised or otherwise non-optimal in which case it is necessary to search for a different reference electrode.

A common method for detecting and removing certain types of EEG artifacts is to break the original signals into individual sources using techniques like CCA and ICA. Then the individual sources are examined to see if the individual sources are likely produced by the types of artifact that have been targeted. If the types of artifact target are the types of artifact of each of the individual sources, then the artifacts are removed and the signals are reconstituted using the remaining sources.

BRIEF SUMMARY OF THE INVENTION

The present invention provides a solution to this problem.

In the present invention, each individual separated source is reconstituted by itself back to an optimal montage and that montage is examined to see whether it is consistent with the artifact being detected. This process is repeated for each of the sources, and any of the sources that are determined to represent the artifact are removed and then the signal is reconstituted from the remaining sources.

The present invention avoids the disadvantages found when trying to recognize the artifact is source space. First, the sign and physical amplitude (e.g., uV) of the source signal are unknown. Secondly, the spatial representation of source signals are highly variable and dependent on the montage and reference used, making recognition of the artifact significantly more difficult.

In one example for an eye blink removal, an epoch is first separated into sources using BSS (blind source separation).

Each source is then reconstituted to the recorded montage and then to a CZ reference montage that is considered optimal for recognizing the eye blink type artifact. The channels of the CZ reference montage are examined by a neural network to determine if it is likely to be any eye blink. If it is, then this particular source is removed and the algorithm moves on to the next source. However, if there was an issue with the CZ electrode, then a different reference electrode would be selected for the source.

One aspect of the present invention is a method for detecting and removing EEG artifacts. The method includes generating an EEG signal. The method also includes separating the EEG signal into a plurality of sources. Each source of the plurality of sources is separated for a selected artifact type. The method also includes reconstituting each source of the plurality of sources into a recorded montage and an optimal reference montage for recognizing the selected artifact type of each source of the plurality of sources. The method also includes examining a plurality of channels of the optimal reference montage for each source of the plurality of sources to determine if the selected artifact type is the true artifact of each source of the plurality of sources. The method also includes determining that the selected artifact type is the true artifact of each source of the plurality of sources. The method also includes removing each source of the plurality of sources for the selected artifact type to generate a plurality of remaining sources. The method also includes reconstituting the plurality of remaining sources into a filtered montage for the EEG signal.

Another aspect of the present invention is a method for detecting and removing EEG artifacts. The method includes separating an epoch of an EEG recording into a plurality of sources utilizing a blind source separation algorithm. Each of the plurality of sources is separated for a selected artifact type. The method also includes reconstituting each source of the plurality of sources into a recorded montage and an optimal reference montage for recognizing the selected artifact type of each source of the plurality of sources. The method also includes examining a plurality of channels of the optimal reference montage for each source of the plurality of sources to determine if the selected artifact type is the true artifact of each source of the plurality of sources. The method also includes determining that the selected artifact type is the true artifact of each source of the plurality of sources. The method also includes removing each source of the plurality of sources for the selected artifact type to generate a plurality of remaining sources. The method also includes reconstituting the plurality of remaining sources into a filtered montage for the EEG signal.

Yet another aspect of the present invention is a method for detecting and removing EEG artifacts. The method includes separating an EEG recording into a plurality of sources, each of the plurality of sources separated for a selected artifact type. The method also includes reconstituting each source of the plurality of sources into a recorded montage and an optimal reference montage for recognizing the selected artifact type of each source of the plurality of sources. The method also includes examining a plurality of channels of the optimal reference montage for each source of the plurality of sources to determine if the selected artifact type is the true artifact of each source of the plurality of sources. The method also includes removing each source of the plurality of sources for the selected artifact type to generate a plurality of remaining sources. The method also includes reconstituting the plurality of remaining sources into a filtered montage for the EEG signal.

Yet another aspect of the present invention is a method for detecting and removing at least two artifacts from an EEG signal. The method includes separating an EEG recording into a plurality of sources. Each of the plurality of sources is separated for a selected artifact type. The method also includes reconstituting a first source of the plurality of sources into a recorded montage and an optimal reference montage for recognizing a first artifact type. The method also includes examining a plurality of channels of the optimal reference montage for the first source of the plurality of sources to determine if the first artifact type is the true artifact of first source of the plurality of sources. The method also includes removing the first source of the plurality of sources for the first artifact type. The method also includes reconstituting a second source of the plurality of sources into a recorded montage and an optimal reference montage for recognizing a second artifact type. The method also includes examining a plurality of channels of the optimal reference montage for the second source of the plurality of sources to determine if the second artifact type is the true artifact of second source of the plurality of sources. The method also includes removing the second source of the plurality of sources for the second artifact type. The method also includes reconstituting a plurality of remaining sources into a filtered montage for the EEG signal.

Yet another aspect of the present invention is a system for detecting and removing EEG artifacts. The system includes electrodes, a processor, and a display. The electrodes generate EEG signals. The processor is connected to the electrodes to generate an EEG recording from the EEG signals. The display is connected to the processor and displays an EEG recording. The processor is configured to separate an EEG signal into a plurality of sources, each source of the plurality of sources separated for a selected artifact type. The processor is configured to reconstitute each source of the plurality of sources into a recorded montage and an optimal reference montage for recognizing the selected artifact type of each source of the plurality of sources. The processor is configured to examine a plurality of channels of the optimal reference montage for each source of the plurality of sources to determine if the selected artifact type is the true artifact of each source of the plurality of sources. The processor is configured to determine that the selected artifact type is the true artifact of each source of the plurality of sources. The processor is configured to remove each source of the plurality of sources for the selected artifact type to generate a plurality of remaining sources. The processor is configured to reconstitute the plurality of remaining sources into a filtered montage for the EEG signal.

Yet another aspect of the present invention is a system for detecting and removing EEG artifacts utilizing a blind source separation algorithm. The system includes electrodes, a processor, and a display. The electrodes generate EEG signals. The processor is connected to the electrodes to generate an EEG recording from the EEG signals. The display is connected to the processor and displays an EEG recording. The processor is configured to separate an epoch of a EEG recording into a plurality of sources utilizing a blind source separation algorithm. Each of the plurality of sources is separated for a selected artifact type. The processor is configured to reconstitute each source of the plurality of sources into a recorded montage and an optimal reference montage for recognizing the selected artifact type of each source of the plurality of sources. The processor is configured to examine a plurality of channels of the optimal reference montage for each source of the plurality of sources to determine if the selected artifact type is the true artifact of each source of the plurality of sources. The processor is configured to determine that the selected artifact type is the true artifact of each source of the plurality of sources. The processor is configured to remove each source of the plurality of sources for the selected artifact type to generate a plurality of remaining sources. The processor is configured to reconstitute the plurality of remaining sources into a filtered montage for the EEG signal.

Yet another aspect of the present invention is a system for detecting and removing at least two artifacts from an EEG signal. The system includes electrodes, a processor, and a display. The electrodes generate EEG signals. The processor is connected to the electrodes to generate an EEG recording from the EEG signals. The display is connected to the processor and displays an EEG recording. The processor is configured to separate an EEG recording into a plurality of sources. Each of the plurality of sources is separated for a selected artifact type. The processor is configured to reconstitute a first source of the plurality of sources into a recorded montage and an optimal reference montage for recognizing a first artifact type. The processor is configured to examine a plurality of channels of the optimal reference montage for the first source of the plurality of sources to determine if the first artifact type is the true artifact of first source of the plurality of sources. The processor is configured to remove the first source of the plurality of sources for the first artifact type. The processor is configured to reconstitute a second source of the plurality of sources into a recorded montage and an optimal reference montage for recognizing a second artifact type. The processor is configured to examine a plurality of channels of the optimal reference montage for the second source of the plurality of sources to determine if the second artifact type is the true artifact of second source of the plurality of sources. The processor is configured to remove the second source of the plurality of sources for the second artifact type. The processor is configured to reconstitute a plurality of remaining sources into a filtered montage for the EEG signal.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
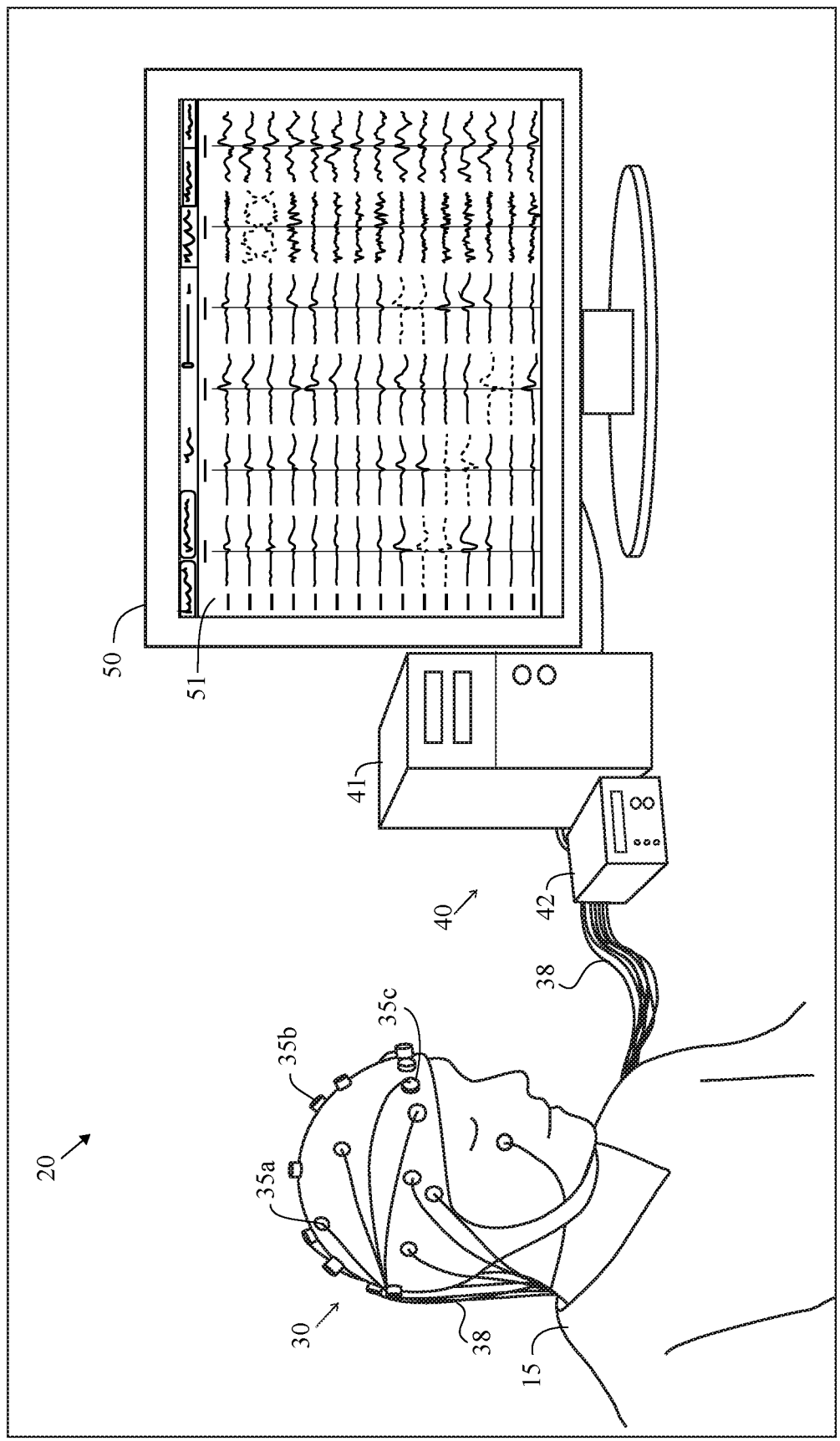
FIG. 1 is a block diagram of a system for analyzing an EEG recording.

As shown in FIG. 1, an EEG system is generally designated 20. The system preferably includes a patient component 30, an EEG machine component 40 and a display component 50. The patient component 30 includes a plurality of electrodes 35a, 35b, 35c attached to the patient 15 and wired by cables 38 to the EEG machine component 40. The EEG machine component 40 comprises a CPU 41 and an amplifier component 42. The EEG machine component 40 is connected to the display component 50 for display of the combined EEG reports, and for switching from a processed EEG report to the combined EEG reports, or from the processed EEG report to an original EEG report.

Figure 7:
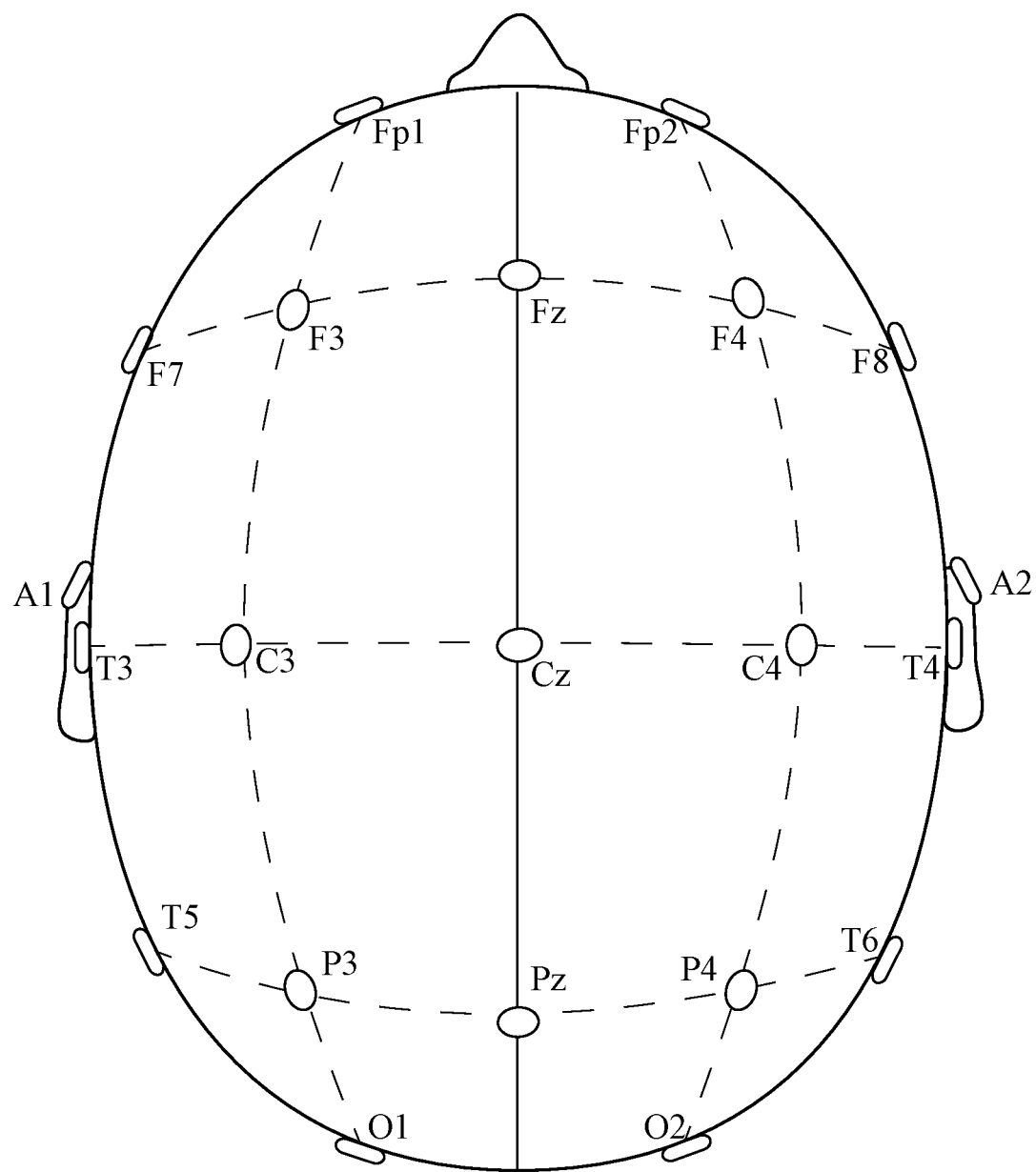
FIG. 7 is a map for electrode placement for an EEG.
Figure 8:
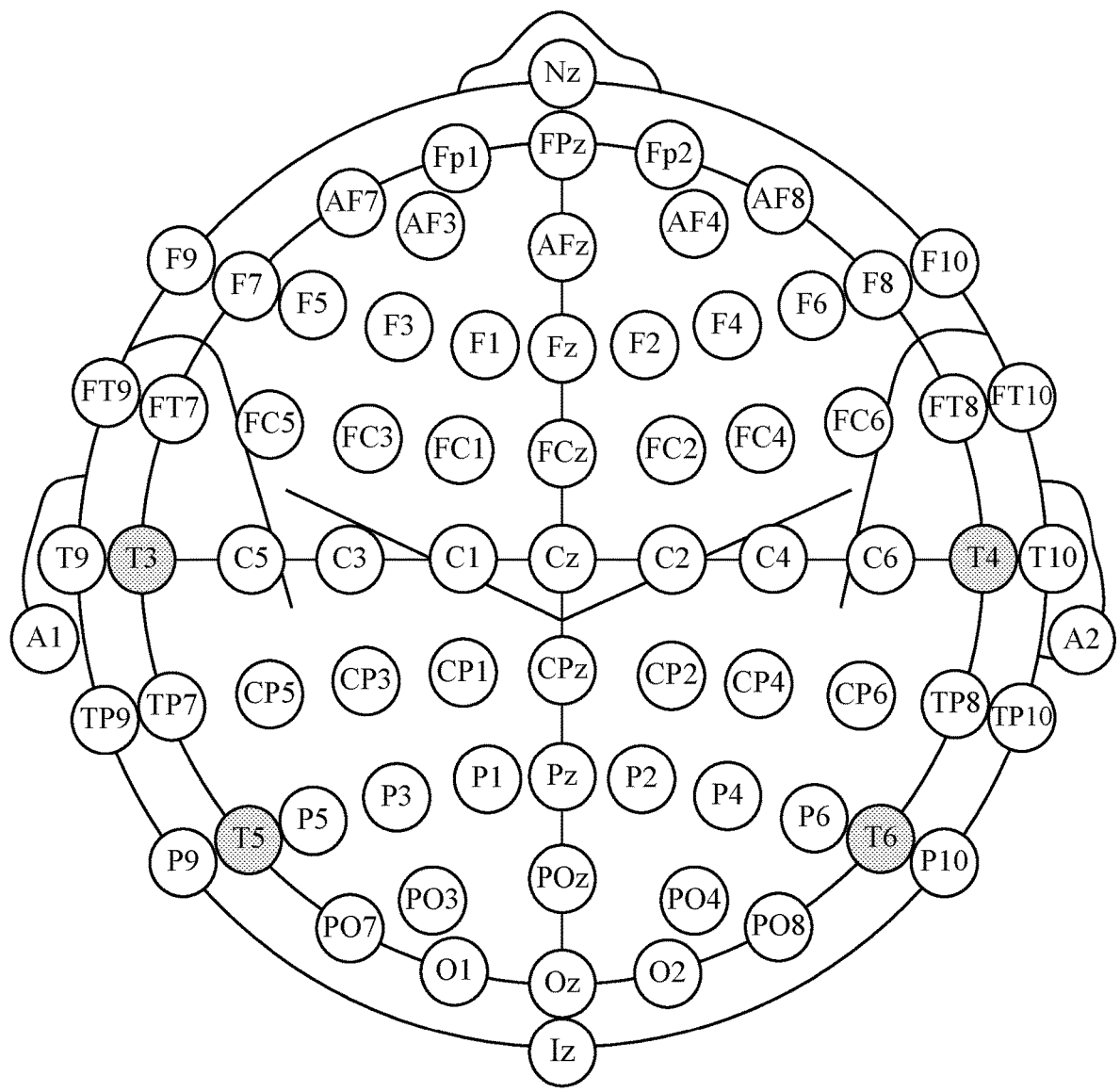
FIG. 8 is a detailed map for electrode placement for an EEG.

A patient has a plurality of electrodes attached to the patient's head with wires from the electrodes connected to an amplifier for amplifying the signal to a processor, which is used to analyze the signals from the electrodes and create an EEG recording. The brain produces different signals at different points on a patient's head. Multiple electrodes are positioned on a patient's head as shown in FIGS. 7 and 8. The CZ site is in the center. For example, Fp1 on FIG. 7 is represented in channel FP1-F3 on FIG. 2. The number of electrodes determines the number of channels for an EEG. A greater number of channels produce a more detailed representation of a patient's brain activity. Preferably, each amplifier 42 of an EEG machine component 40 corresponds to two electrodes 35 attached to a patient's 15 head. The output from an EEG machine component 40 is the difference in electrical activity detected by the two electrodes. The placement of each electrode is critical for an EEG report since the closer the electrode pairs are to each other, the less difference in the brainwaves that are recorded by the EEG machine component 40. A more thorough description of an electrode utilized with the present invention is detailed in Wilson et al., U.S. Pat. No. 8,112,141 for a Method And Device For Quick Press On EEG Electrode, which is hereby incorporated by reference in its entirety. The EEG is optimized for automated artifact filtering. The EEG recordings are then processed using neural network algorithms to generate a processed EEG recording, which is analyzed for display.

Algorithms for removing artifact from EEG typically use Blind Source Separation (BSS) algorithms like CCA (canonical correlation analysis) and ICA (Independent Component Analysis) to transform the signals from a set of channels into a set of component waves or "sources."

FIGS. 2-6 illustrate analyzed EEG recordings. An additional description of analyzing EEG recordings is set forth in Wilson et al., U.S. patent application Ser. No. 13/620,855, filed on Sep. 15, 2012, for a Method And System For Analyzing An EEG Recording, which is hereby incorporated by reference in its entirety.

Figure 2:
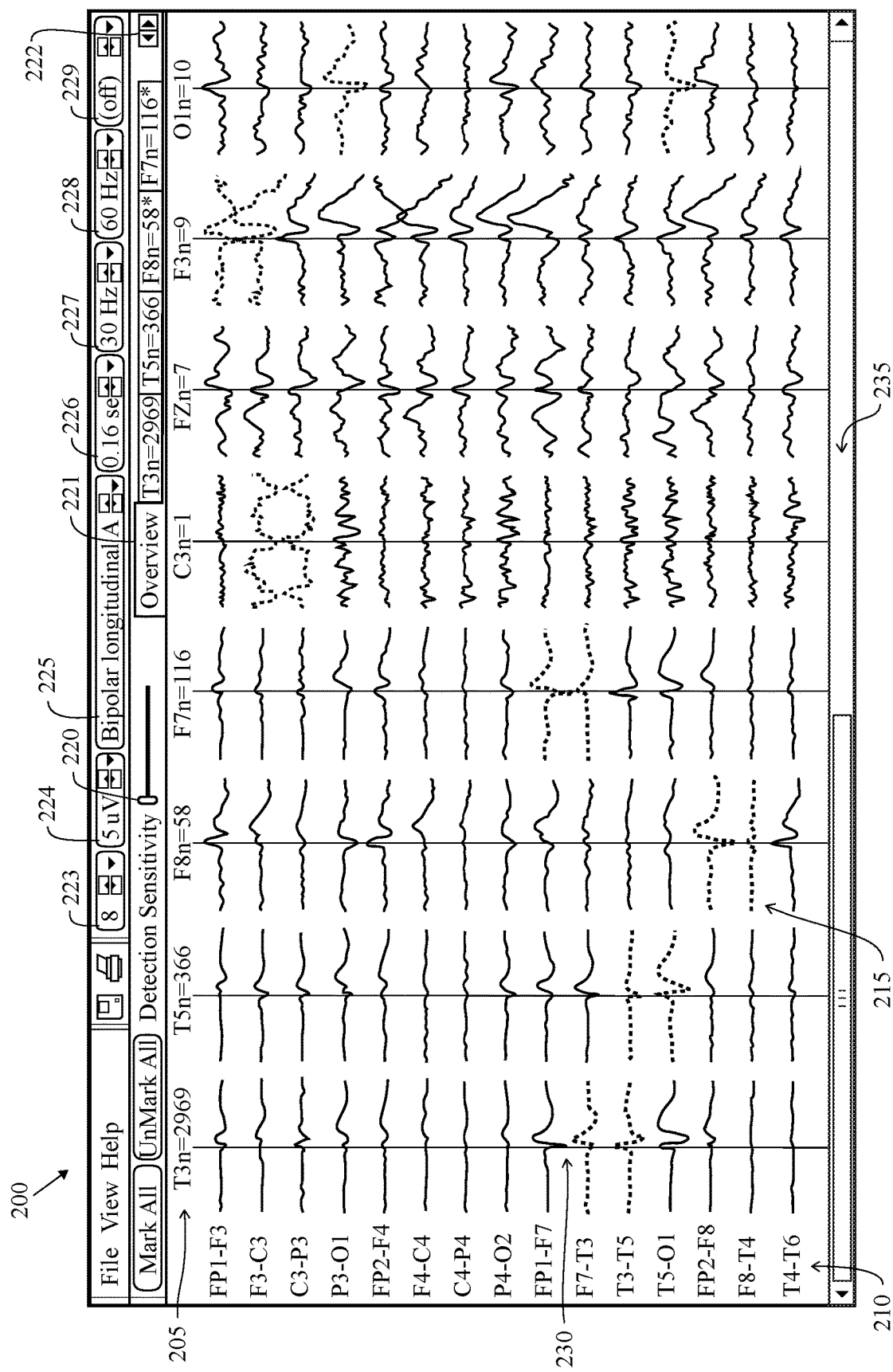
FIG. 2 is an illustration of an analyzed EEG recording.
Figure 3:
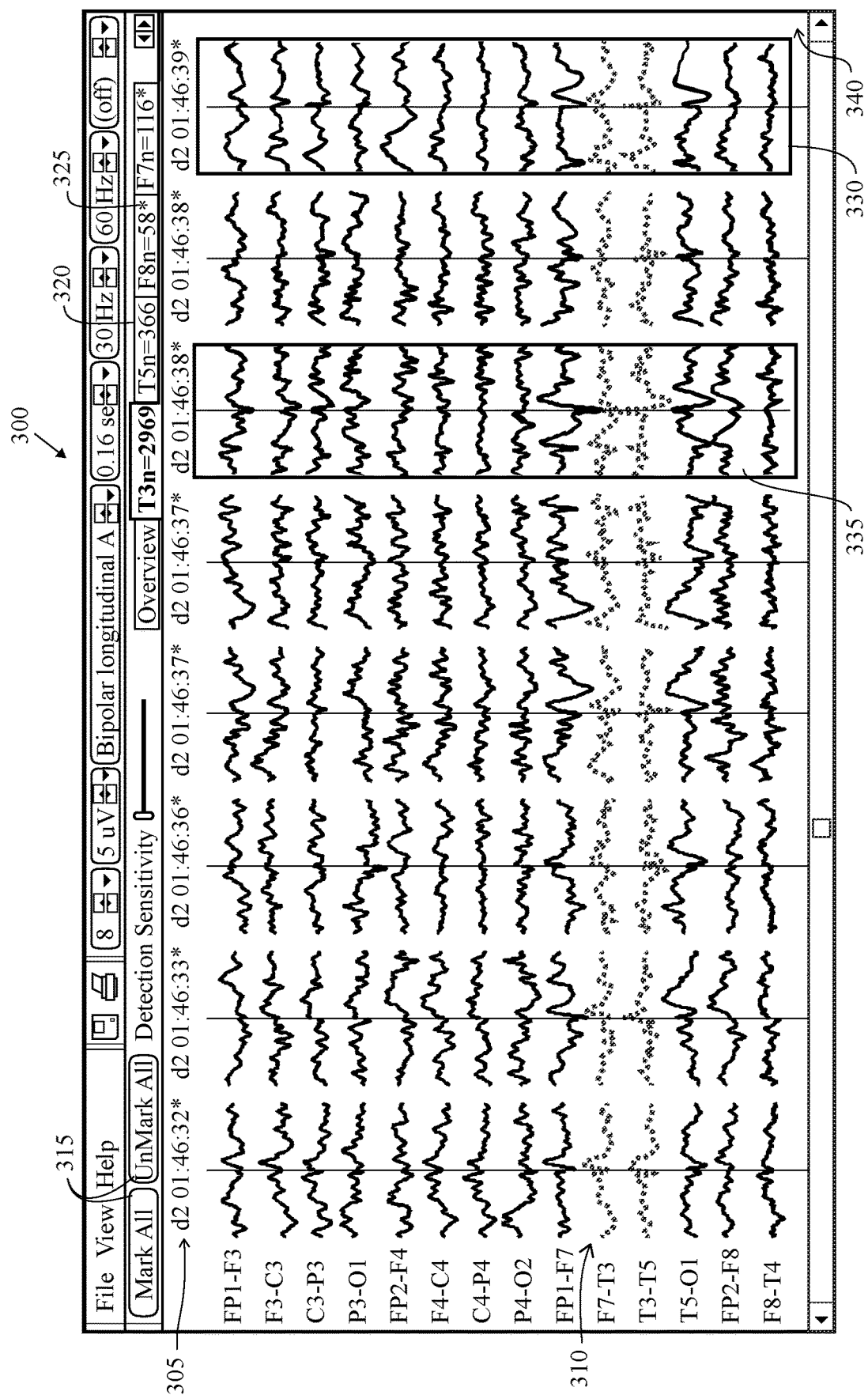
FIG. 3 is an illustration of an analyzed EEG recording.

When the Easy SpikeReview program opens, the Overview window 200 is initially presented, as shown in FIG. 2. The overview depicts averages from the various spike foci detected by a spike detection mechanism. To create these overview averages the spike detections are sorted by detection foci (electrode) and then all detections at a particular focus are mathematically averaged. For example, the first column of EEG represents an average of 2969 events that had their maximum point of detection at the T3 electrode. The columns of the EEG are preferably separated from other columns by a thin band of white. Each EEG column represents a distinct group average. The primary electrode focal point of each average, and the number of detection events incorporated into each average, 205 are shown above the columns of EEG. Channels including the detection focal point electrode are highlighted red 215. As with evoked potentials, averaging multiple detections results in an increase in the signal-to-noise ratio and makes it easier to delineate the field of distribution of epileptiform abnormalities.

The various functions of the Easy SpikeReview window include the ability to choose spike detections per page 223, an EEG voltage amplitude selector 224, a montage selector 225, LFF (TC) 226, HFF 227, notch 228, and a custom filter 229. Navigation to other tabs not in the current view is also possible with the forward and back tabs 222. If there's more than one page of Overview averages, clicking on the bottom bar 230 will page forward. Right-clicking on the montage bar 210 will show montage controls.

The sensitivity of the SpikeDetector output can be dynamically adjusted during the review process, which is done by using the detection sensitivity slider 220 that is labeled. When Easy SpikeReview is initially opened, the detection sensitivity slider 220 is set to the far left position. In this position the SpikeDetector neural network algorithms identify sharp transients that have a high probability of being epileptiform abnormalities: these are events the detector assigned a high probability of being a real epileptiform abnormality. The rate of false positive detections at this setting is lowest. Thus, the ratio of true epileptiform signal to false positive noise is highest at this setting. However, some spikes and sharp waves that are less well-formed may not be evident with the slider set at its lowest sensitivity. The detector's sensitivity can be quickly adjusted by dragging the slider 220 towards the right so that it is more sensitive and thus more likely to identify less well-formed or lower amplitude transients. New groups may then appear in the overview display of spike averages. In concert with the increase in true spike detections, there is also an increase in false positive detections.

In records with rare epileptiform abnormalities or those in which the SpikeDetector neural networks, when set to lowest sensitivity, do not recognize the epileptiform abnormalities well, switching to the highest setting on the detection sensitivity slider 220 may allow visualization of real epileptiform abnormalities. In such cases, identifying the rare events often requires assessment of the individual raw detections. This is accomplished by either displaying all raw detections back-to-back following the spike averages on the overview page, or by reviewing the detections at each electrode location, such as in FIG. 3, by progressively selecting the location tabs 221 at the top of the EEG window. Detections that have already been viewed are marked with a trailing asterisk 325 behind the time.

Figure 4:
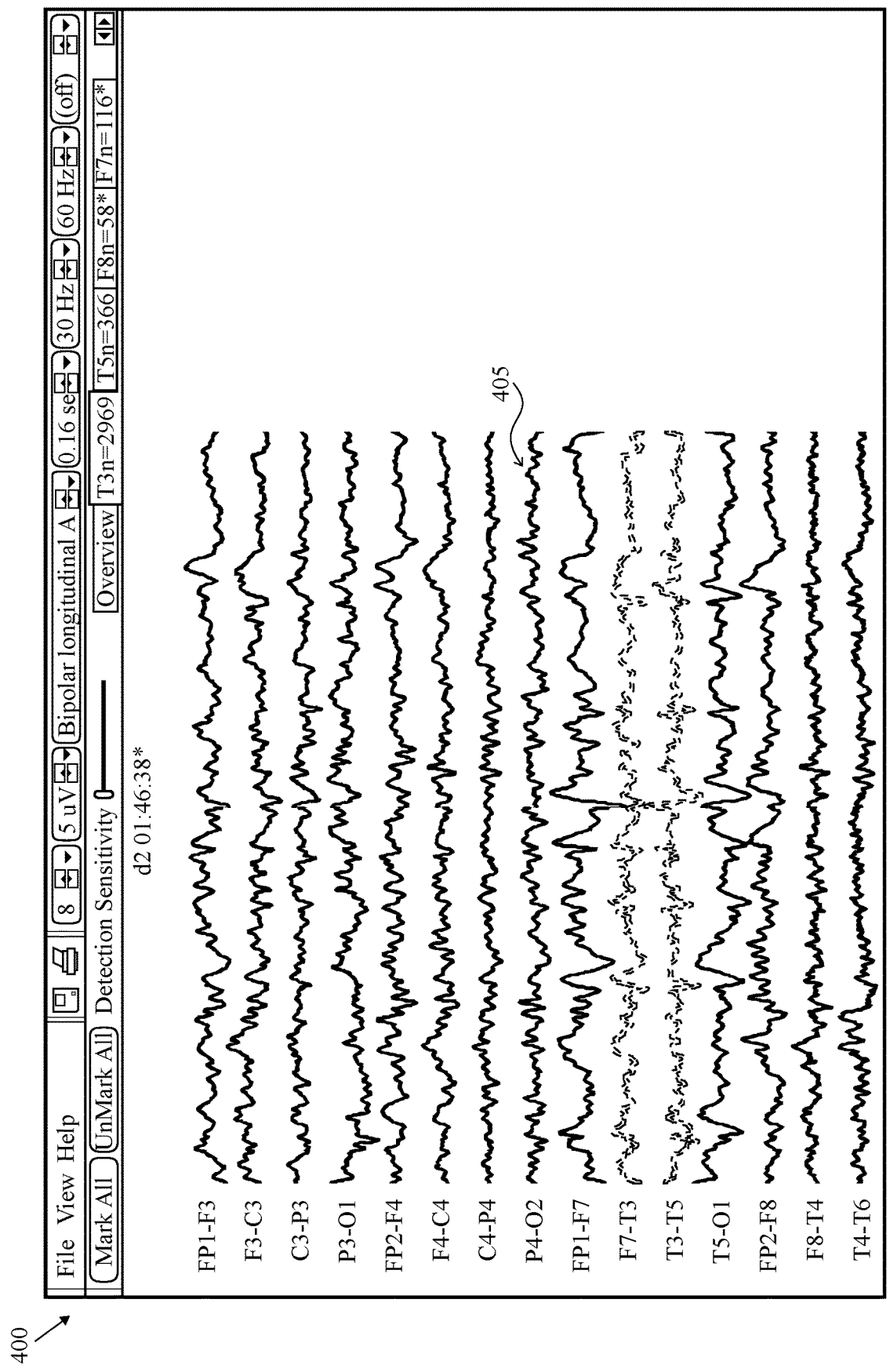
FIG. 4 is an illustration of an analyzed EEG recording.

Clicking on any of the electrode location tabs 221 at the top of the EEG window will display the raw (non-averaged) spike detections 300 that arose from that particular electrode location. The individual detections are separated by a thin band of white, and the detection point is centered in a one second segment of EEG and indicated by a faint vertical gray line with a heading indicating the time of detection 305. Channels containing the electrode involved in the detection are highlighted red 310. Left double-clicking with the mouse on any individual detection 335 will cause an expanded EEG view 400, as shown in FIG. 4, of that particular detection 335 to appear. Left double-clicking on the expanded view 400 will return the user to a display of back-to-back individual detections 300.

When viewing individual spike detections (accessed from the tabs 221 above the EEG window), exemplar spikes can be hand-marked by left-clicking with the mouse on the desired example. A rectangle outlining the chosen spike 330 will appear. Marking all or unmarking all detections can be done with the Mark All or UnMark All buttons 315 on the toolbar. Hand-marked detections will be included in the spike averages that appear in the FinalReport.

Figure 5:
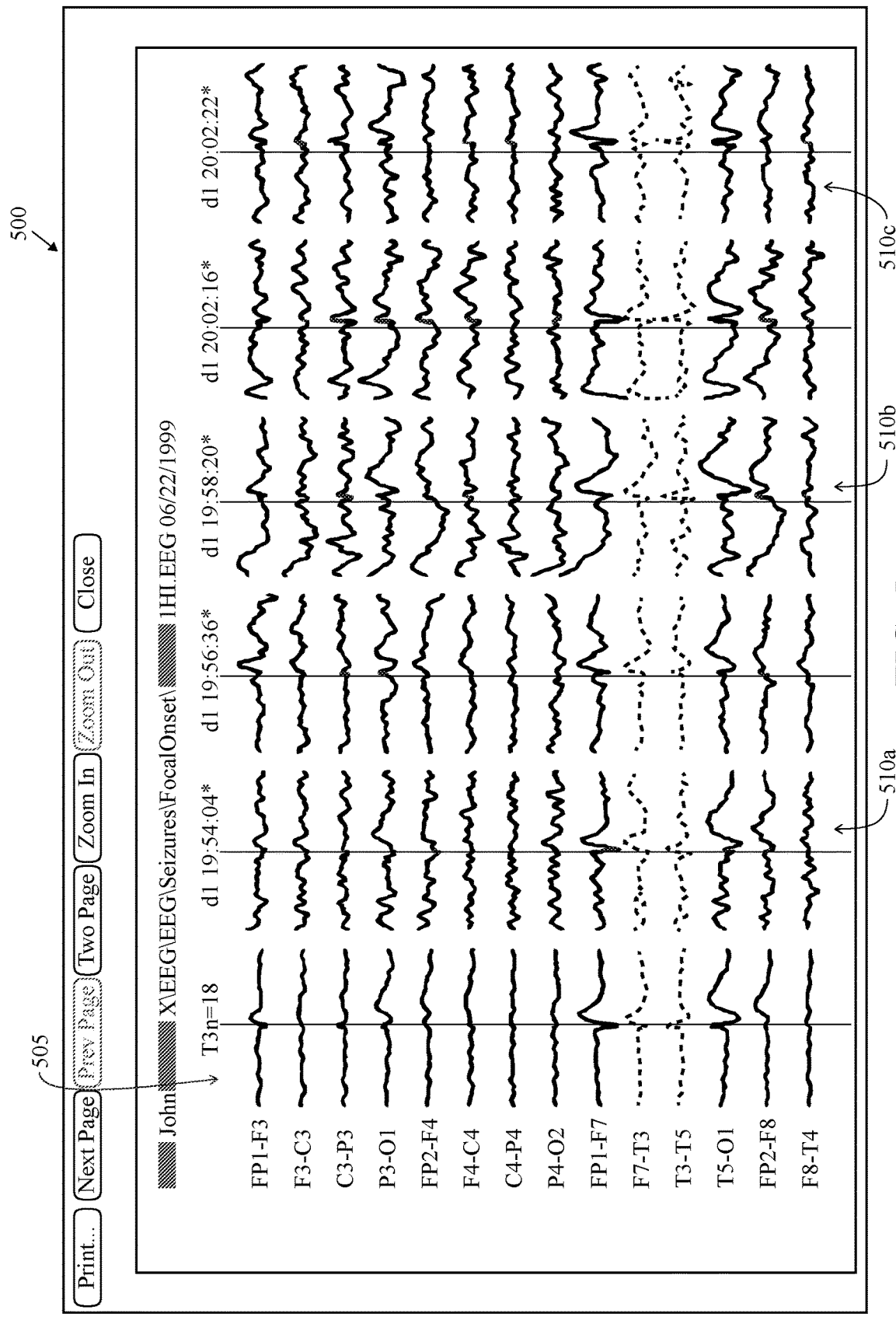
FIG. 5 is an illustration of an analyzed EEG recording.

FIG. 5 is a print preview view 500 of a FinalReport showing a group average of 18 user-selected spikes 505 and constituent spikes 510a-510c.

Figure 6:
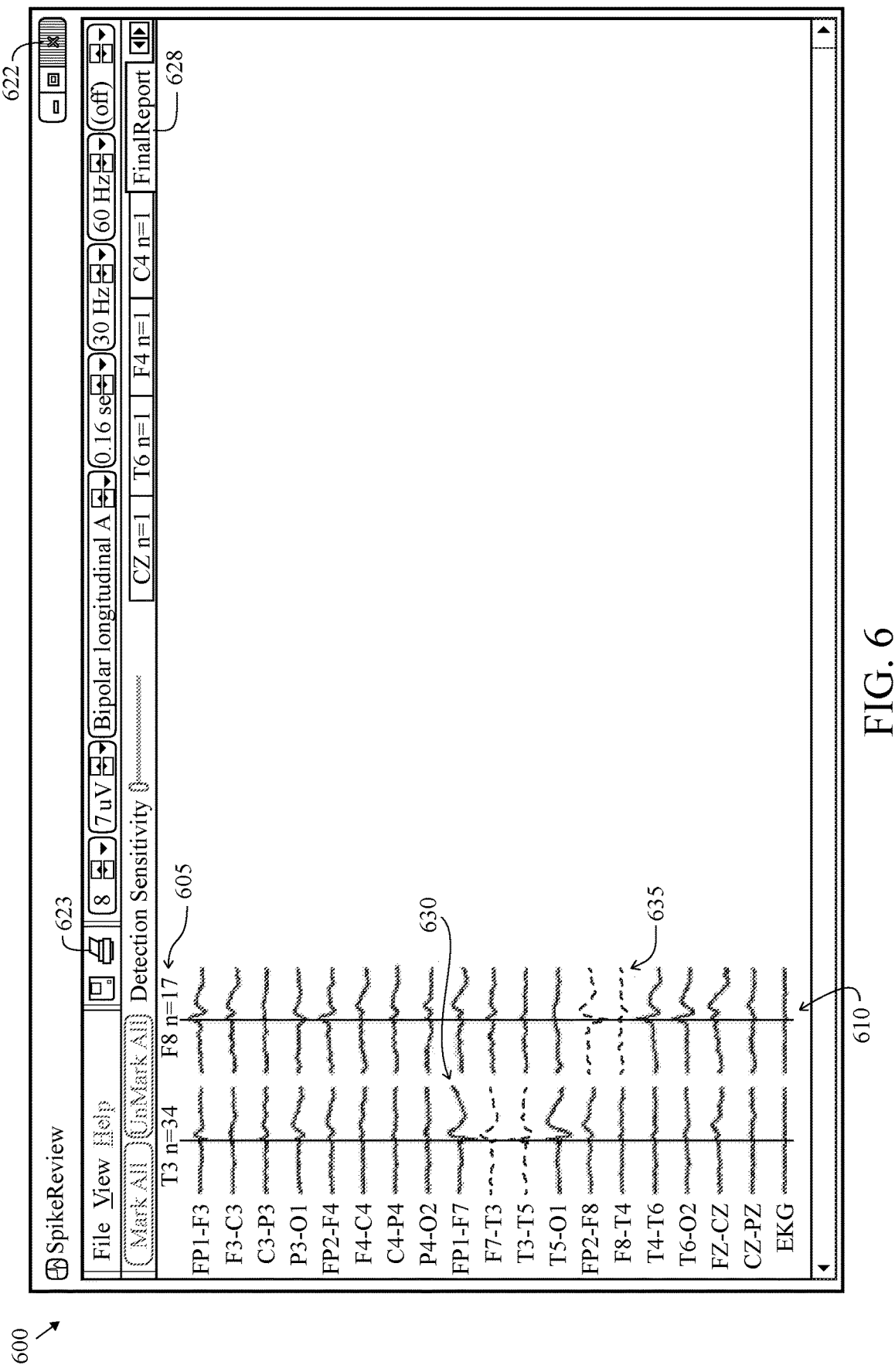
FIG. 6 is an illustration of an analyzed EEG recording.

These hand-marked events can also be displayed back-to-back, as shown in FIG. 6, immediately following their averages in FinalReport 600, and can be printed 623 for archival purposes or for evaluation by another reviewer.

Clicking on FinalReport tab 628 at the top of the EEG window displays a summary of all hand-marked exemplar spike or sharp waves 610 at the focus 605 chosen. The initial default view shows the mathematical averages of the user-chosen hand-marked events, sorted by electrode focus 605. As explained, head voltage topograms and back-to-back individual user-selected events are displayed by selecting menu options or via right mouse click choices. Voltage topograms are only created when viewing the EEG in a referential montage. Also illustrated in FIG. 6 are ser chosen spikes and waves 630, and view/jumpt to spikes 635.

Upon exiting 622 the program, all changes are automatically saved, including user marked spikes and viewed events.

Figure 11:
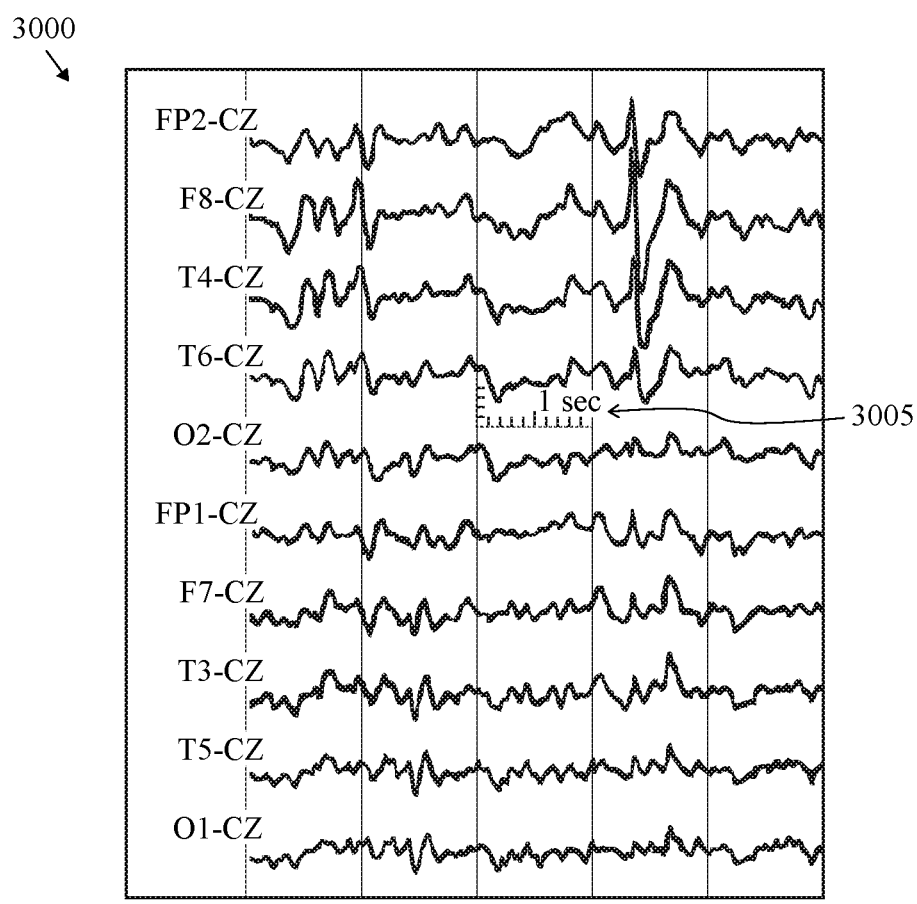
FIG. 11 is an illustration of a CZ reference montage.

FIG. 11 is an illustration of an EEG recording 3000 with CZ reference montage 3005.

In one example an algorithm called BSS-CCA is used to remove the effects of muscle activity from the EEG. Using the algorithm on the recorded montage will frequently not produce optimal results. In this case it is generally optimal to use a montage where the reference electrode is one of the vertex electrodes such as CZ in the international 10-20 standard. In this algorithm the recorded montage would first be transformed into a CZ reference montage prior to artifact removal. In the event that the signal at CZ indicates that it is not the best choice then the algorithm would go down a list of possible reference electrodes in order to find one that is suitable.

It is possible to perform BSS-CCA directly on the user-selected montage. However this has two issues. First this requires doing an expensive artifact removal process on each montage selected for viewing by the user. Second the artifact removal will vary from one montage to another, and will only be optimal when a user selects a referential montage using the optimal reference. Since a montage that is required for reviewing an EEG is frequently not the same as the one that is optimal for removing artifact this is not a good solution.

Figure 9:
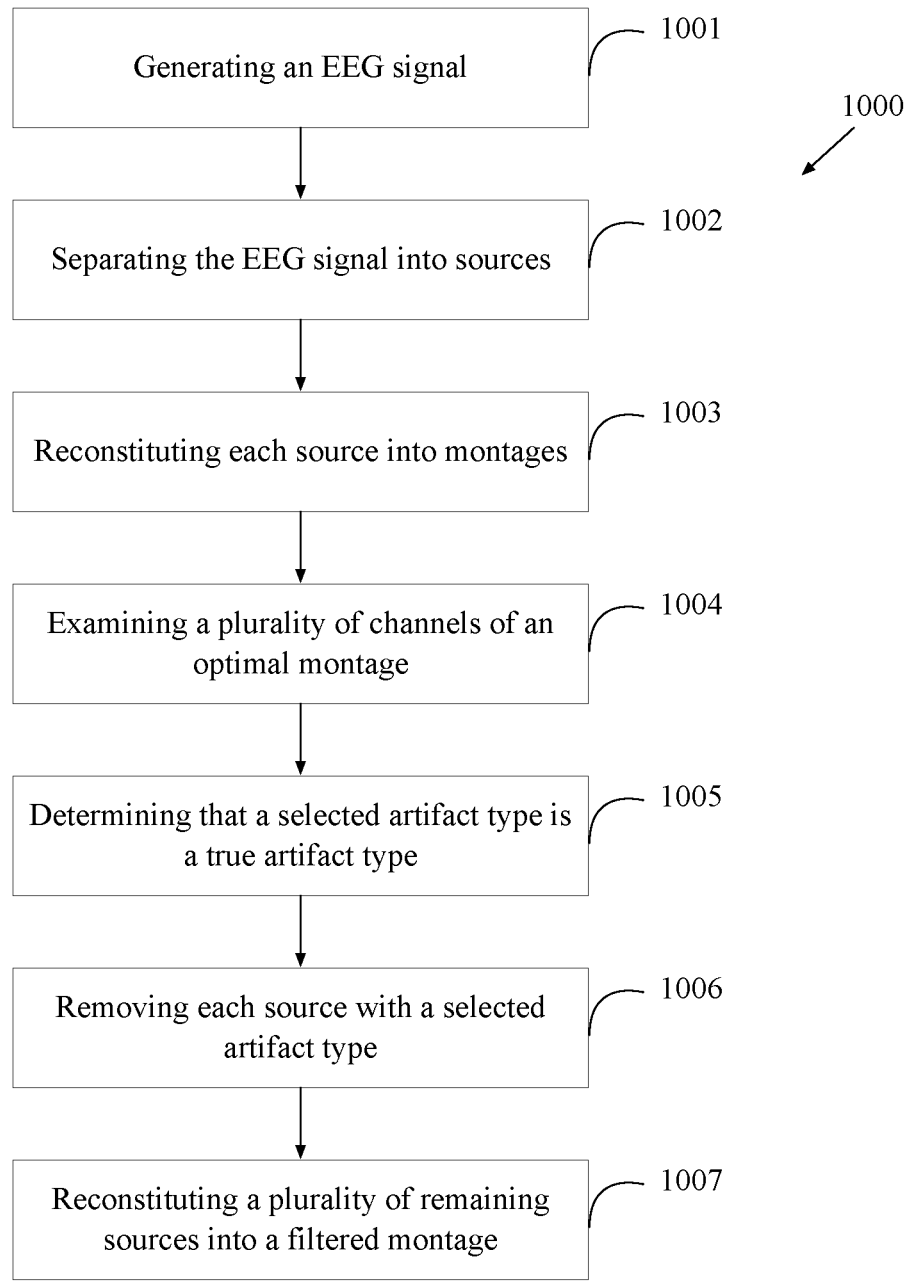
FIG. 9 is a flow chart of a general method to optimize automated artifact filtering for an EEG based.

FIG. 9 is a flow chart of a general method 1000 for detecting and removing EEG artifacts. At block 1001, an EEG signal is generated. At block 1002, the EEG signal is separated into a plurality of sources. Each source of the plurality of sources is separated for a selected artifact type. At block 1003, each source of the plurality of sources is reconstituted into a recorded montage and an optimal reference montage for recognizing the selected artifact type of each source of the plurality of sources. At block 1004, the channels of the optimal reference montage for each source of the plurality of sources are examined to determine if the selected artifact type is the true artifact of each source of the plurality of sources. At block 1005, the selected artifact type is determined to be the true artifact of each source of the plurality of sources. At block 1006, each source of the plurality of sources for the selected artifact type is removed to generate a plurality of remaining sources. At block 1007, the remaining sources are reconstituted into a filtered montage for the EEG signal.

The artifact removal algorithm is preferably a blind source separation algorithm. The blind source separation algorithm is preferably a CCA algorithm or an ICA algorithm.

Figure 10:
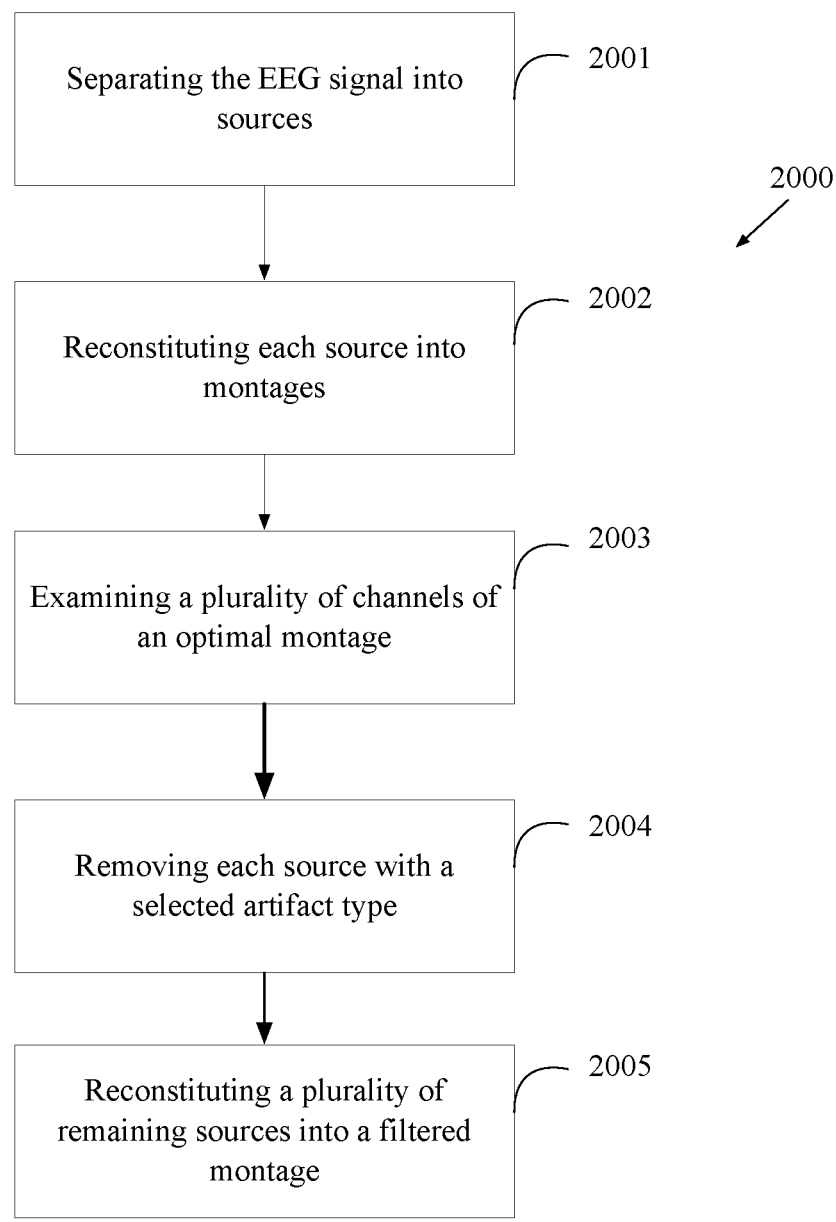
FIG. 10 is a flow chart of a specific method to optimize automated artifact filtering for an EEG based.

FIG. 10 is a flow chart of a general method 2000 for detecting and removing EEG artifacts. At block 2001, the EEG signal is separated into a plurality of sources. Each source of the plurality of sources is separated for a selected artifact type. At block 2002, each source of the plurality of sources is reconstituted into a recorded montage and an optimal reference montage for recognizing the selected artifact type of each source of the plurality of sources. At block 2003, the channels of the optimal reference montage for each source of the plurality of sources are examined to determine if the selected artifact type is the true artifact of each source of the plurality of sources. At block 2004, each source of the plurality of sources for the selected artifact type is removed to generate a plurality of remaining sources. At block 2005, the remaining sources are reconstituted into a filtered montage for the EEG signal.

Figure 12:
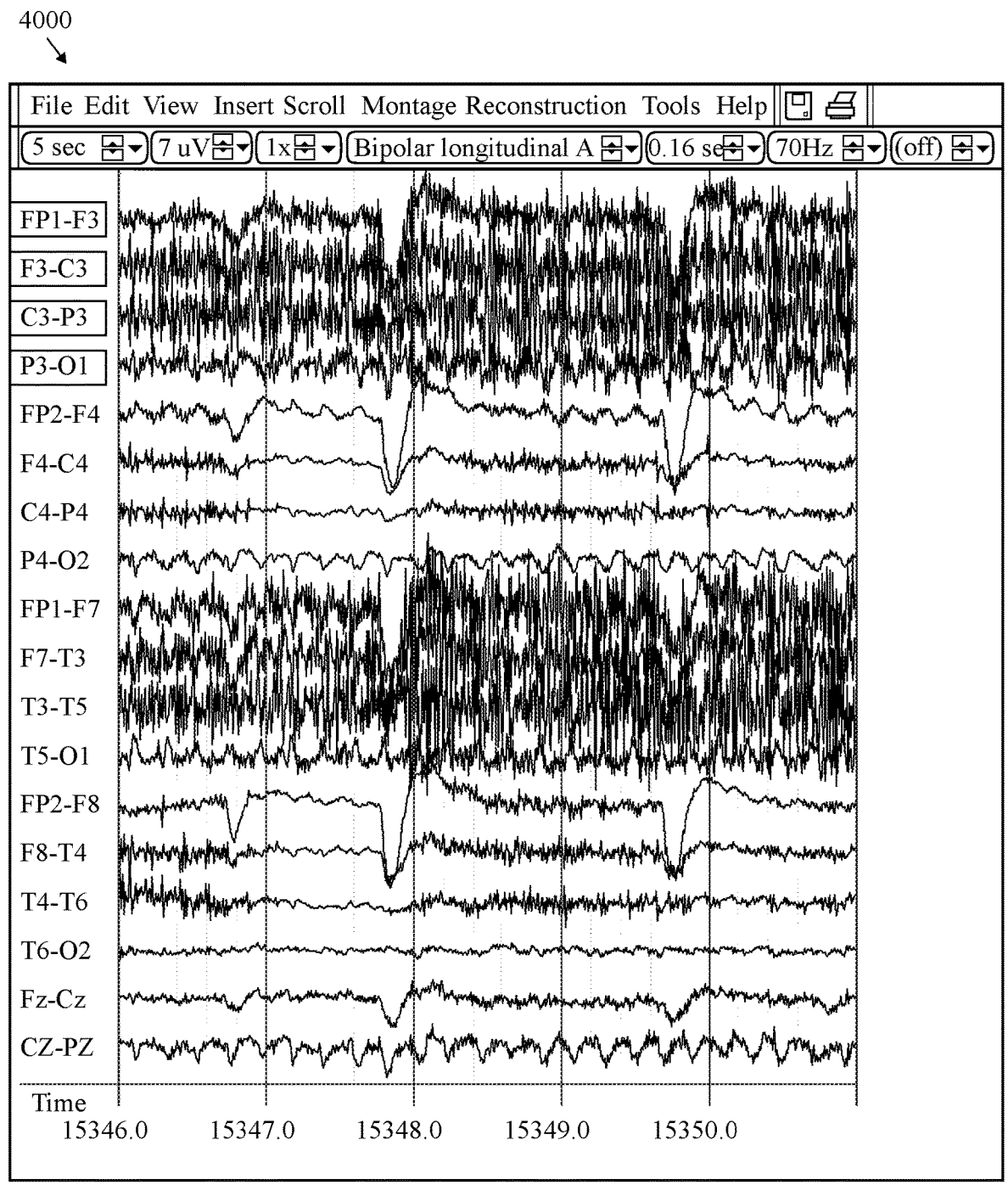
FIG. 12 is an illustration of an EEG recording containing a seizure, a muscle artifact and an eye movement artifact.
Figure 13:
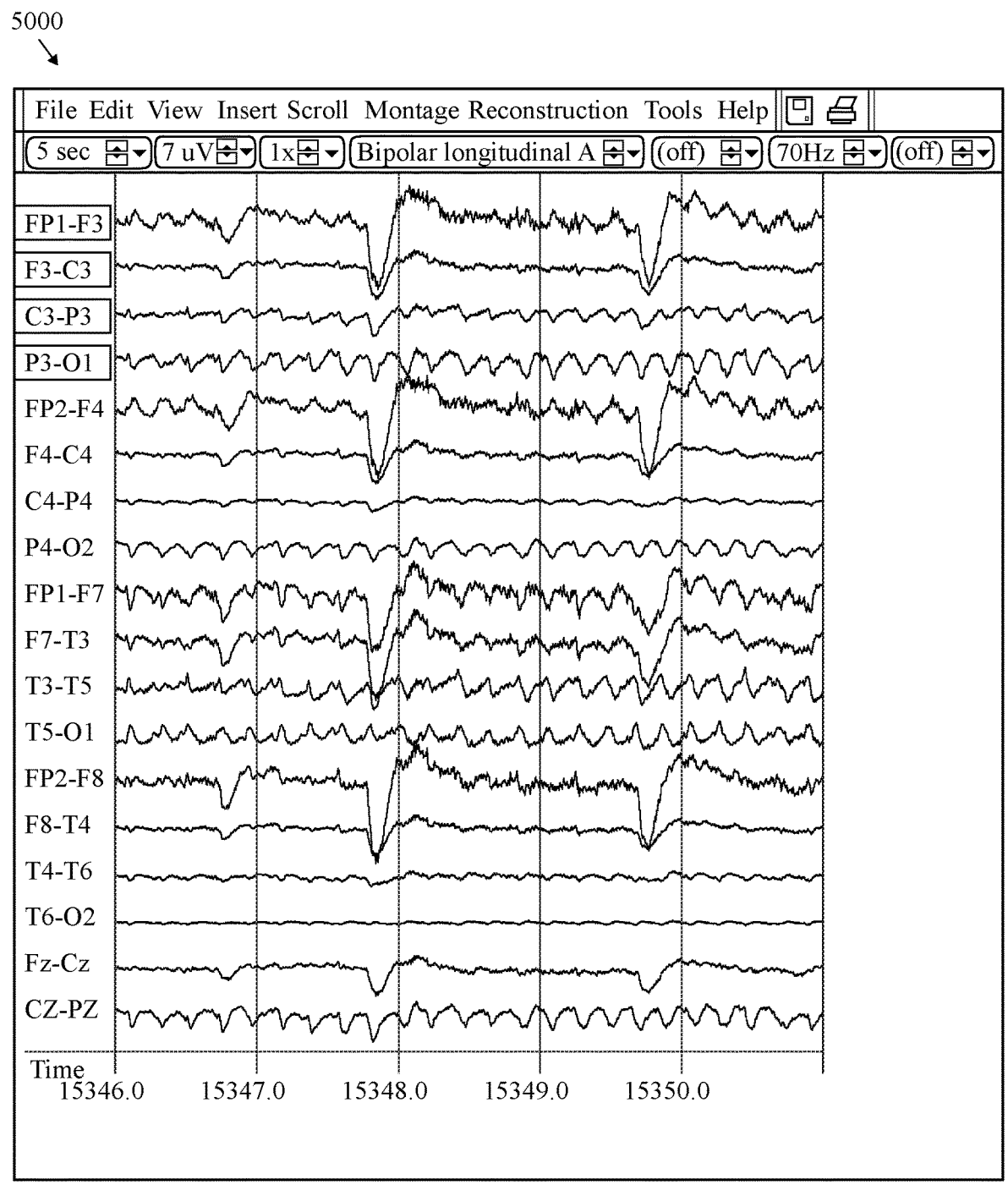
FIG. 13 is an illustration of the EEG recording of FIG. 12 with the muscle artifact removed.
Figure 14:
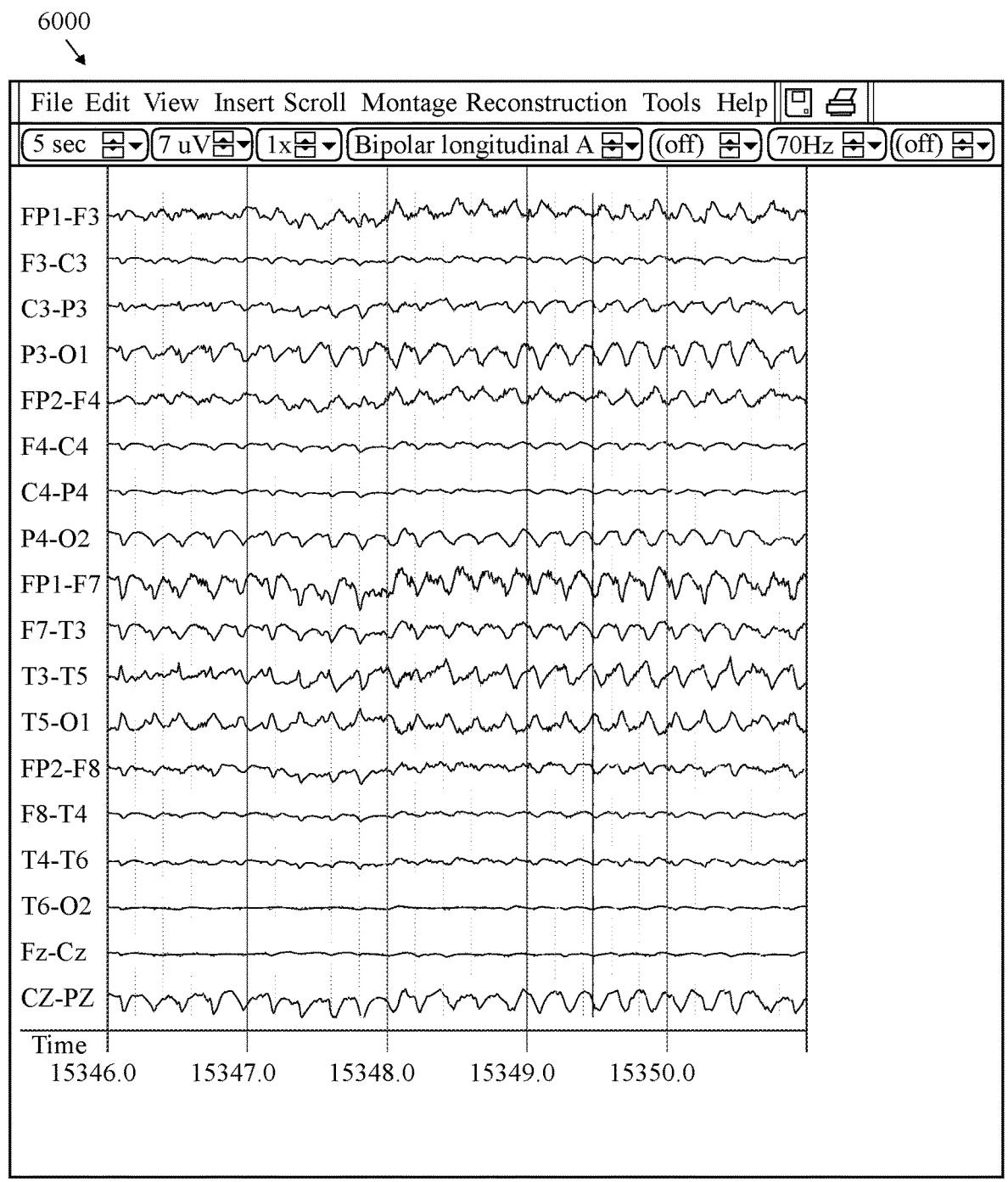
FIG. 14 is an illustration of the EEG recording of FIG. 13 with the eye movement artifact removed.

FIGS. 12-14 illustrate how removing artifacts from the EEG signal allow for a clearer illustration of a brain's true activity for the reader. FIG. 12 is an illustration of an EEG recording 4000 containing a seizure, a muscle artifact and an eye movement artifact. FIG. 13 is an illustration of the EEG recording 5000 of FIG. 12 with the muscle artifact removed. FIG. 14 is an illustration of the EEG recording 6000 of FIG. 13 with the eye movement artifact removed From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim.

Therefore, the embodiments of the invention in which an exclusive property or privilege is claimed are defined in the following appended claims.

We claim as our invention:

1. A method for processing an electroencephalogram ("EEG") recording to generate a filtered montage for an EEG signal, the method comprising:

separating, by a processor, an epoch of an original EEG recording using a blind source separation to generate a plurality of sources for the original EEG recording wherein a sign and physical amplitude of a source signal of the plurality of sources is unknown, each of the plurality of sources separated for an eye blink artifact removal, the original EEG recording generated by an EEG machine component comprising a CPU, an amplifier component, and a plurality of electrodes attached to a patient's head, wherein the plurality of electrodes comprises 10-20 electrodes with a CZ reference electrode;

reconstituting, by the processor, a first source of the plurality of sources to generate a recorded montage and an optimal reference montage for recognizing the eye blink artifact type;

examining, by the processor using a neural network, a plurality of channels of the optimal reference montage for the first source to determine if the eye blink artifact type is the true artifact of the first source;

removing, by the processor, the first source of the plurality of sources for the eye blink artifact type;

reconstituting, by the processor, a second source of the plurality of sources into a recorded montage and an optimal reference montage for recognizing a muscle artifact type;

examining, by the processor using the neural network, a plurality of channels of the optimal reference montage for the second source to determine if the muscle artifact type is the true artifact of the second source;

removing, by the processor utilizing blind source separation-canonical correlation analysis, the second source for the muscle artifact type;

reconstituting, by the processor, a plurality of remaining sources into a filtered montage for the EEG signal; and displaying the filtered montage for the EEG signal on a graphical user display for a clearer illustration of a brain activity of the EEG signal than the original EEG signal wherein the muscle artifact type and the eye-blink artifact type are removed in the filtered montage.

\* \* \* \* \*